United States Patent [19]

Saurat et al.

[11] Patent Number: 5,438,073
[45] Date of Patent: Aug. 1, 1995

[54] DERMATOLOGICAL AND/OR COSMETOLOGICAL COMPOSITION CONTAINING RETINOIDS

[75] Inventors: Jean-Hilaire Saurat, Geneve; Georges Siegenthaler, Bellevue, both of Switzerland; Henri Cousse, Pins Justaret, France; Gilbert Mouzin, Toulouse, France; Yvon Gall, Portet sur Garonne, France

[73] Assignee: Pierre Fabre Cosmetique, Boulogne, France

[21] Appl. No.: 211,384

[22] PCT Filed: Oct. 1, 1992

[86] PCT No.: PCT/FR92/00908

§ 371 Date: Mar. 31, 1994

§ 102(e) Date: Mar. 31, 1994

[87] PCT Pub. No.: WO93/06818

PCT Pub. Date: Apr. 15, 1993

[30] Foreign Application Priority Data

Oct. 1, 1991 [FR] France .................. 91 12044

[51] Int. Cl.$^6$ .............. A61K 31/335; A61K 31/13; C07D 319/06; C07D 317/00; C07C 233/00; C07C 251/00
[52] U.S. Cl. .................. 514/452; 514/467; 514/641; 549/369; 549/372; 549/453; 549/454; 564/191; 564/193; 564/271; 564/276
[58] Field of Search .............. 549/369, 372, 453, 454; 564/191, 193, 276, 271; 514/452, 467, 641

[56] References Cited

U.S. PATENT DOCUMENTS

| | | | |
|---|---|---|---|
| 4,523,042 | 6/1985 | Loev et al. | 568/824 |
| 4,614,747 | 9/1986 | Loev et al. | 514/529 |
| 4,722,939 | 2/1988 | Loev et al. | 514/529 |
| 5,093,360 | 3/1992 | Yu et al. | 514/463 |

OTHER PUBLICATIONS

Mackenroth et al., Chem. Abst., 117-251057 (1992).
Jaeger et al., Chem. Abst., 119:130925 (1993).

*Primary Examiner*—Cecilia Tsang
*Attorney, Agent, or Firm*—Dressler, Goldsmith, Shore & Milnamow, Ltd.

[57] ABSTRACT

Dermatological and/or cosmetological compositions containing at least one retinoid of general formula (I), and the use of such compounds for preparing dermatological and/or cosmetological compositions.

14 Claims, No Drawings

DERMATOLOGICAL AND/OR COSMETOLOGICAL COMPOSITION CONTAINING RETINOIDS

This application is a 371 of PCT/FR92/009081, filed Oct. 1, 1992.

The present invention relates to compositions for topical use which are, in particular, useful in dermatology and/or in cosmetology, as well as to the use of new retinoids for preparing such compositions. It also relates to a new group of retinoid derivatives.

In effect, it is commonly accepted that retinol, or (ROL), is essential for vision, reproduction, growth and cell differentiation; on the other hand, retinoic acid (or RA) is involved only in the regulation and control or differentiation of cell growth (Wolf. G., Physio. Rev. 64, p. 873–937; 1984);

Retinoic acid is present in plasma at a level approximately 150 times lower than that of retinol (Deleenhefr et al., J. Lipid. Res., 23, p. 1362 to 1367, 1982).

In addition, retinoic acid is rapidly eliminated from the body, suggesting that this acid is formed from retinol, close to the site of its biological action. Retinoic acid may be formed by enzymatic oxidation in two steps. During this process, retinol is oxidized to retinal, which is subsequently oxidized to retinoic acid. These two steps require the presence of cofactor NAD. Recent studies have shown the presence of an enzyme system which is capable of converting retinol to retinoic acid in certain tissues of rodents, such as the kidney and liver of rats, or the skin of mice (Connor M. J. et al., Biochem J., 244, p. 489–492, 1987).

However, these studies have not elucidated the question of the specificity of the enzyme systems involved with respect to their substrates: all these tissues contain high levels of alcohol and aldehyde dehydrogenases, which are capable of non-specifically oxidizing a large number of alcohols and aldehydes, including retinol and retinal.

These studies have not shown whether the dehydrogenases involved in the oxydation of ROL→RA in the natural metabolism of the retinoids are different from those involved in the metabolism of alcohol.

The origin of the retinoic acid utilized in epidermal cells is still being debated at the present time.

One source may be the retinoic acid in the plasma; however, owing to the fact that it is rapidly metabolized and eliminated, it is probable that the retinoic acid is formed enzymatically from retinol at its site of action. However, the studies of the prior art have not been able to elucidate the exact nature of the enzyme system involved.

The mechanism of action of retinoic acid and of its analogues in the cell brings into play nuclear receptors belonging to the superfamily of thyroxosteroidal hormone receptors which act as retinoic acid-inducible factors for genomic transcription (Krust A. et al., Proc. Natl., Acad. Sci., U.S.A., 86, 5310–5314, 1989). However, the analogy between the mode of action of thyroxo-steroid hormones and that of retinoic acid is not complete. In effect, retinoic acid in tissues requires an intracellular transporter protein, or CRABP (Cellular Retinoic Acid-Binding Protein), which probably acts as a carrier for transporting its ligand from the cytoplasm to the nucleus.

Retinoic acid is the active metabolite of retinol in certain specific functions (cell differentiation), because retinoic acid is much more active than retinol in the control of cell differentiation, suggesting that the conversion of retinol to retinoic acid would be partly responsible for the activity attributed to retinol. This is one of the reasons why retinoic acid or its analogues have been selected as therapeutic agents.

Moreover, Creek et al., (J. Invest. Dermatol., 92, p. 283–289, 1989), have shown that retinol supplied to the extracellular medium was metabolized to (inactive) retinol esters by keratinoctes [sic] in culture. Ottonello S. et al., (J. Biol. Chem., 262, p. 3975–3981, 1987) have shown that the plasma membrane of the target cells of retinoids possessed an extremely active enzyme system, which was capable of esterifying retinol in order to deactivate it and store it in the membranes. As a result, there is every reason to think that entry of retinol into the cell is limited by a very active control mechanism which proceeds via esterases. These facts explain the low efficacy of retinol as a therapeutic agent in dermatology.

Retinoic acid has thus been used, under the name "vitamin A acid", for example in Application EP 230 498, in compositions intended for combating light-induced aging of the skin.

The retinoids used in dermatology are traditionally all-trans-retinoic acid and analogues such as (13Z)-retinoic acid, acitretin, arotinoic acid, and the like, and have a genuine biological activity. However, they also possess considerable side effects, irrespective of whether they are used systemically or topically, and in particular induce a strong local irritation.

Related compounds have been used in various compositions. Thus, EP 339 905 describes cicatrizing compositions containing a combination of at least one polypeptide growth factor and at least one retinoid.

EP 71 537 describes pharmaceutical compositions in which a linolenic acid or an equivalent is necessarily combined with a vitamin A type product, for the treatment of allergic and inflammatory disorders.

The use of new intermediates in the biosynthesis of retinoic acid or of their analogues, by short-circuiting the metabolism of activation of retinol to retinoic acid in the cell, makes it possible to obtain molecules having different affinities with respect to the nuclear receptors for retinoic acid, and an activity of their own which is not identical to that of retinoic acid.

Thus, the subject of the present invention is a dermatological and/or cosmetological composition, characterized in that it contains at least one retinoid of general formula (I)

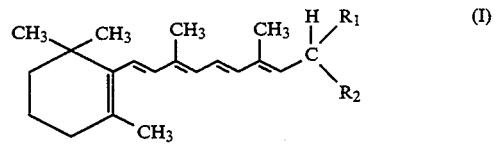

in which:
$R_1$ and $R_2$ independently represent

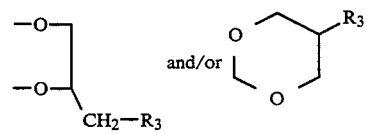

or $R_1$ and $R_2$ together represent a double bond with an oxygen atom, or with a nitrogen atom so as to form an imine group of formula $=N-R_4$, $R_3$ represents a hydrogen atom, a hydroxyl group or an acyloxy group containing 5 carbon atoms, $R_4$ represents a group chosen from:

$-CH_2-(CH_2)_n-O-R_5$, or

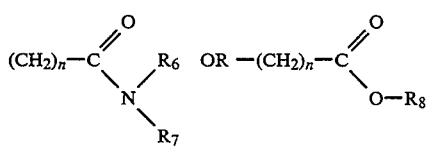

with n ranging from 0 to 5, $R_5$ represents a hydrogen atom, a lower alkyl group having 1 to 5 carbon atoms or a lower acyl group having 1 to 5 carbon atoms, $R_6$ and $R_7$ independently represent a hydrogen atom or a lower alkyl group having 1 to 5 carbon atoms, $R_8$ represents a hydrogen atom or a lower alkyl group having 1 to 5 carbon atoms.

The compounds corresponding to the formula I belong to the group of bioprecursors of retinal.

Retinal and/or its bioprecursors may be oxidized to retinoic acid or reduced to retinol by enzyme systems which are particular to each cell.

The bioprecursors of retinal may be oxidized to retinoic acid and/or converted to retinol in the case of retinal and of these [sic] acetals, using intracellular enzymes of the epidermal cells of retinoid metabolism. The use of one or more substances, according to the present invention, makes it possible to influence and to control the metabolism of the natural retinoids, because the cell does not have a membrane mechanism which blocks their entry. Moreover, they have a much less acute toxicity than retinoic acid or its analogues, which also allows their use in cosmetology.

Since the metabolism is highly regulated, bringing a retinal bioprecursor into contact with epidermal cells results in the biosynthesis of reinoic [sic] acid and/or retinol, which are themselves pharmacologically active.

The compositions which are a subject of the present invention will be useful for the treatment of certain dermatological and/or cosmetological disorders, without displaying the side effects of the substances used in the prior art, such as retinoic acid and its analogues, or the lack of efficacy of retinol.

In effect, the enzyme system converts retinol to retinoic acid, may be used as an important step in regulation of the cell metabolism, acting upstream of the nuclear receptors [sic].

The compounds of formula I are thus seen to be pharmacologically active intermediate products. The tissues, depending on their various enzymatic activities, will be able to convert the compounds of formula I either to retinoic acid or to retinol, depending on their specific needs.

The retinoic acids act directly on the genome via the nuclear receptors. As a result, the cell has little possibility of influencing the action of the retinoids hitherto used, apart from the level of nuclear receptors, their catabolism or their bioavailability (membrane permeability), which might be responsible for the side effects (cheilitis, dermatitis and the like).

Preferred bioprecursors are those against which the target cell has no membrane mechanisms which form a barrier to entry. Retinal may, in its turn, be metabolized to retinoic acid and/or retinol. An advantage of these bioprecursors is that they modify the overall kinetics of the biosynthesis of retinoic acid and/or of retinol, which provides an additional pharmacological means of control.

The bioprecursors used according to the present invention are the acetal derivatives of general formula I, and more particularly the cyclization derivatives with glycerol in position 1-2 or 1-3.

Thus, according to one of its aspects, the subject of the present invention is a composition for topical use, characterized in that it contains the 1-2 cyclic acetal of glycerol of formula (II)

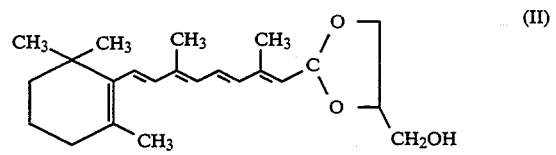

According to another of its aspects, the subject of present invention is a composition for topical use, characterized in that it contains the acetylated derivative of the 1-2 cyclic acetal of glycerol of formula (III).

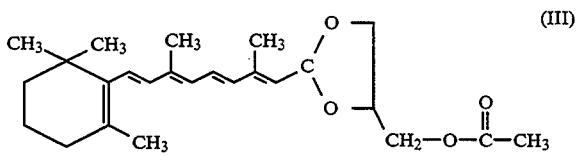

According to yet another of its aspects, the subject of the present invention is a topical composition, characterized in that it contains the 1-3 cyclic acetal of glycerol of formula (IV)

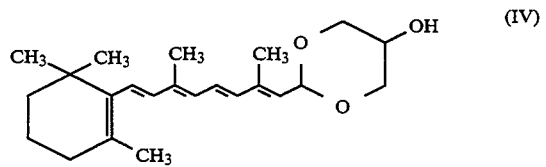

Other particularly advantageous compositions according to the present invention contain imines with aminoethanol or glycinamide, corresponding to the formulae:

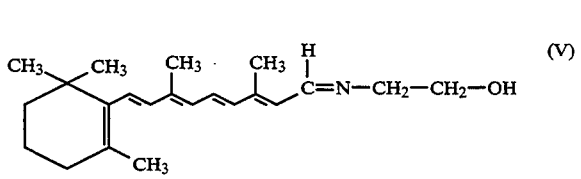

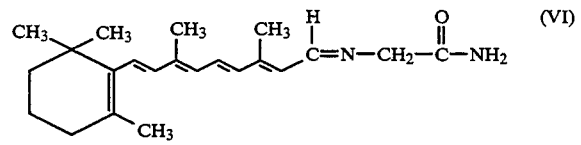

The compositions according to the present invention are, in particular, useful in dermatology, in stomatology and/or in cosmetology.

The dermatological and/or stomatological compositions according to the present invention preferably contain from 0.01 to 5% by weight of at least one retinoid of formula I.

The retinoid is preferably present in the composition at a concentration of between 0.1 and 1% by weight.

The retinoids of formula (I) are, in one of the embodiments of the invention, used for the manufacture of a dermatological composition intended for the treatment of complaints chosen from the group comprising: psoriasis, acne, eczema, rosacea, actinic keratosis, seborrheic dermatitis, congenital keratinization disorders.

In this respect, retinal is particularly well suited to the preparation of compositions intended for the treatment of acne rosacea or of seborrheic dermatitis.

Rosacea manifests itself, in particular, by the presence of blotches on the face. Seborrheic dermatitis is characterized by an inflammatory manifestation with peeling of the scalp, of the face and possibly of other regions of the body.

The application of a composition containing retinal to patients having these complaints makes possible a marked improvement of the symptoms observed.

Another use of the retinoids of formula (I) according to the present invention, is for the preparation of a stomatological composition which is useful in the treatment of complaints affecting the mucosae, particularly the buccal mucosae.

According to another of its aspects, the subject of the present invention is a cosmetological composition, characterized in that it contains from 0.01 to 5% by weight, and preferably from 0.1 to 1%, of a retinoid of formula I, in a cosmetologically acceptable vehicle.

One of the subjects of the present invention is thus the use of at least one retinoid compound of formula I as defined above, for the preparation of a cosmetological composition which is, in particular, useful for the treatment of disorders due to aging and/or of seborrhea.

In effect, an exogenous supply of retinal to a target cell will considerably modify the redistribution of retinol and its esters, as well as the retinoic acid level inside the cell. In addition, this redistribution will be made according to the enzymatic activities particular to the cell. The Applicant has shown that these activities differ according to the phase of development of one and the same cell in a tissue, or alternatively according to the types of cells or of tissues. In addition, the cell may also control the degradation of the retinoic acid thus produced in order to prevent any undesirable diffusion to other cells.

This new technique avoids the systematic drenching of a tissue or body with retinoic acid or its analogues, without giving the cells the possibility of controlling, by their individual metabolism, the production of metabolites which they require, for example retinol or retinoic acid. The use of the retinoids according to the present invention as pharmacologically active precursors makes it possible for the cell itself to control its retinol or retinoic acid levels according to the needs of the moment.

The compositions which are the subject of the present invention will thus have a beneficial effect, not only on psoriasis, but also on any complaint responding to a treatment with retinoic acid, in particular any complaint linked to cell differentiation, such as, for example, light-induced aging of the skin or precancerous skin conditions, without displaying the side effects of retinoic acid.

Thus, the subject of the present invention is also the compounds of general formula I

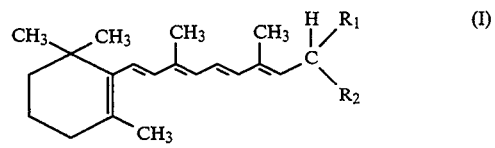

in which:
$R_1$ and $R_2$ independently represent

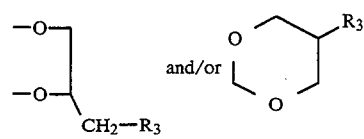

or $R_1$ and $R_2$ together represent a double bond with an oxygen atom, or with a nitrogen atom so as to form an imine group of formula $=N-R_4$, $R_3$ represents a hydrogen atom, a hydroxyl group or an acyloxy group containing 5 carbon atoms, $R_4$ represents a group —$CH_2$—$(CH_2)n$—O—$R_5$, or

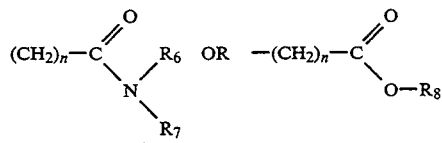

with n ranging from 0 to 5, $R_5$ represents a hydrogen atom, a lower alkyl group having 1 to 5 carbon atoms or a lower acyl group having 1 to 5 carbon atoms, $R_6$ and $R_7$ independently represent a hydrogen atom or a lower alkyl group having 1 to 5 carbon atoms, $R_8$ represents a hydrogen atom or a lower alkyl group having from 1 to 5 carbon atoms.

The examples which follow are intended to illustrate the invention without in any way limiting its scope.

EXAMPLE 1: IN VITRO TESTS

We have measured the conversion of retinol to retinoic acid. We have also measured the enzymatic oxidation-reduction of retinal in human epidermal cell extracts in vitro (HPLC analysis of the products obtained by incubation of cytosol extracts with $^3$H-labeled RAL and ROL).

The HPLC analyses of the retinoids are carried out by the following technique:

A 100 μl aliquot of the cytosol fraction of keratinocytes is incubated with 600 μM ($^3$H) retinol or ($^3$H) retinal for 1 hour.

The reaction is stopped by adding 100 μl of ethanol.

5 μl of internal standard solution containing 4-oxoretinoic acid, all-trans-retinoic acid, 13-cis-retinoic acid, retinol and retinal are subsequently added to the reaction medium.

The radioactive material is then extracted with 3×1 ml of hexane.

The organic phase is collected and completely evaporated using a stream of nitrogen gas.

The residue is subsequently taken up in 50 μl of acetonitrile and analysed on an HPLC column.

The HPLC system consists of a VARIAN 5000 apparatus equipped with an ODS-Ultrasyl reverse-phase column (10 μm, 25×0.4 cm).

The isocratic elution system consists of a mixture of solvents composed of 71% acetonitrile, 23% of ammonium acetate buffer (50 mM, pH 7) and 6% tetrahydrofuran, with a flow rate of 2.4 ml/min.

The unlabeled retinoids are detected by their absorbance measured at 340 nm. 600 μl fractions are also collected using a fraction collector, and their radioactivity is measured with a scintillation counter after adding 4 ml of Pico-fluor.

By using physiological concentrations of retinol, it is shown that cytosol extracts of human keratinocytes, differentiated in culture, were capable of converting retinol to retinoic acid with an enzymatic activity of 4.49+0.17 pmol/h/mg of protein, whereas the cytosol extracts of human keratinocytes which were undifferentiated in culture showed no detectable activity (the keratinocytes are cultured by the technique of Rheinwald-Green, Cell., 6, p. 331–334, 1975; differentiation is controlled using exogenous Ca++).

Furthermore, the Applicant has shown that the protein extract of psoriasis plaques was also capable of converting retinol to retinoic acid, but with a lower activity (0.33+0.07 pmol/h/mg) than differentiated keratinocytes.

On the other hand, cytosol extracts of normal human skin showed no measurable degree of conversion. These differences in the conversion activity may be attributed to the differences in biological activity of the tissues studied or to their different state of differentiation.

This difference in activity between normal skin and the psoriasis plaque could have a pathological significance, and finds application in the manufacture of medicaments; in effect, the psoriasis plaque responds positively to treatment with RA and with retinoids which are retinoic acid analogues.

The activity of this enzyme system in human epidermal cells differs from that which metabolizes alcohol.

In effect, the Applicant has shown that the production of retinoic acid from retinol is not affected by specific inhibitors of alcohol metabolism, such as 4-methylpyrazole and disulfiram, or by an excess of ethanol.

Another experimental fact showing the specificity of this system in epidermal cells is that the cytosol of undifferentiated keratinocytes, despite the presence of an alcohol dehydrogenase activity of the same level as in the cytosol of differentiated keratinocytes, is not capable of forming retinoic acid.

Undifferentiated keratinocytes have no retinol dehydrogenase activity, whereas they are capable of reducing retinal to retinol. The first step in the conversion of retinol could be governed by two different enzymes, each working in one direction (reduction or oxidation), or else a single enzyme capable of working reversibly are/is [sic] responsible for the first step of oxidation of retinol.

The general mechanism is outlined below:

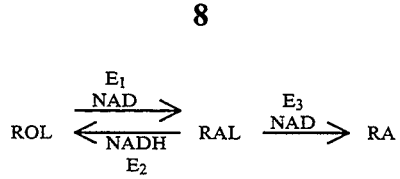

Great differences may be seen between the enzymatic activities E₁, E₂ and E₃ if the activities of a normal skin are compared with a pathological skin or with epidermal cells (keratinocytes) in culture.

On the basis of the general metabolism of natural retinoids in the skin, it is observed that retinal (RAL) plays a central role.

In effect, depending on the ratio of the cofactors AND/NADH, RAL may be converted either to RA or to retinol, depending on the need of the cell. Consequently, the biological message will also be different. Furthermore, RAL seems to be a very active metabolite, because it has not hitherto been detected (very low level) in tissues, whereas it appears to be an intermediate metabolite in the production of RA from ROL.

Analysis of the metabolism of retinals shows that, in epidermal cells, retinal may be either reduced to retinol or oxidized to retinoic acid. The direction of the reaction being influenced by the ratio of the cofactors AND/NADH which participate in the enzymatic oxidation-reduction mechanisms. [sic] Thus, it has been shown that in the presence of NADH, retinal is reduced with the same enzymatic activity in extracts of differentiated cells as in extracts of undifferentiated cells (8 pmol/h/mg), whereas the oxidation of retinal is much greater in extracts of differentiated cells (51.6 pmol/h/mg) than in extracts of undifferentiated cells.

The Applicant has shown that extracts of normal human skin and of the psoriasis plaque are capable of oxidizing retinal to retinoic acid with the same activity, at the rate of 1.35+0.4 pmol/h/mg. However, the psoriasis plaque reduces retinal to retinol twice as quickly (2.5+0.2 pmol/h/mg) as normal skin (1.0+0.3 pmol/h/mg). These observations reveal the central role of retinal as an intermediate metabolite, either in the formation of retinol or in the formation of retinoic acid, and the possibility of using RAL for inducing the biosynthesis either of ROL or of RA.

Retinal must be a very important and decisive metabolite, because it is found in trace quantities in tissues (it is detected, but in immeasurably low concentrations, in embryonic tissues (TALLER et al., Development. 103, p. 473–483, 1988) [lacuna] and is undetectable in adult tissues (NAPOLI et al., J. Biol. Chem., 263, p. 17372–17377, 1988 and CONNOR et al., Biochem. Pharmacol., 36, p. 919–924, 1987), even in animals treated with sizeable doses of retinol.

Not only is retinal the intermediate metabolite of the oxidation of retinol to retinoic acid, but it is also a metabolite of the cleavage of beta-carotene. Beta-carotene is a provitamin A whose vitamin A activity is explained by its conversion to retinal. NAPOLI et al. (J. Biol. Chem., 263, p. 17372–17377, 1988) have shown that rat tissue extracts (kidneys, lungs, liver and intestines) converted beta-carotene to retinol rather than to retinoic acid, but could not demonstrate the presence of retinal as an intermediate metabolite.

The demonstration of retinal in this conversion could only be effected after the partial purification of 15, 15′-beta-carotene dioxygenase. These results show the importance of the step of conversion of retinal to retinol, either for its storage in the form of esters or for any other specific biological action in the membrane, as a second messenger, and the like.

EXAMPLE 2: IN VIVO TESTS

1. Application of retinal to normal human skin.

This test, carried out on 30 healthy volunteers, was intended to evaluate the existance of a biological effect and the tolerance after topical application of retinal.

Three concentrations, 1.0%, 0.1% and 0.05%, were used, in daily covered applications for at least 15 days and up to 3 months in 10 subjects.

The tolerability of the 0.1% and 0.05% preparations is excellent; no irritation was noted, nor any sign of dermatitis caused by the retinoids as is observed with topically applied retinoic acid in concentrations at and above 0.01%. There was, however, a biological effect, which was reflected in a better appearance of the skin, similar to that observed after the topical use of RA in so-called "anti-aging" indications.

The 1% preparation induced a yellowish coloration: an irritation arose in only 10% of cases, which is markedly different from what is observed with RA in such concentrations.

This indicates that retinal may, in effect, be used in very high therapeutic concentrations, and that at lower concentrations it exerts an analogous effect of a "cosmetological" type which is different from that of retinoic acid, without inducing irritations.

2. Application to psoriasis plaques

The 0.1% and 0.05% preparations had only a modest effect on psoriasis plaques in an initial pilot study (these low concentrations have, however, a potentiating effect on the action of UVA). For this reason, the 1% preparation was used and the effects of a daily application were compared with those of the excipient, in 12 patients.

The application was "open" in 6 cases, and with occlusion in six 6. 11 cases were able to be evaluated (5 with occlusion, 6 open). The effect was measured by standard methods (erythema 0-3, squama 0-3, infiltration 0-3), comparing the plaques treated with retinal with the symmetrical plaques treated with the excipients. Photographs were taken at each inspection.

In the series treated with occlusion, the results were very clear: in 3 of the 5 cases, a disappearance of the squamae and a decrease in infiltration with a regression of the lesion score by more than 50% were observed from the first week; in one case the result was good (30% regression of the score), in one case it was modest (10% regression); the plaques treated with the excipient remained unchanged. In the open series, only one very good result was noted, with one good and four modest results.

An important observation was the occurrence of an inflammation specifically localized on the psoriasis plaque following the keratolytic effect and previous [sic] the improvement in infiltration.

This indicates a biological effect which is specifically localized at the site of the psoriatic process.

Conclusions drawn from the teretinalsts

On the basis of the results reported above, retinal performs a central role in human epidermal cells in the intracellular formation of retinol and of retinoic acid. Two possibilities exist for increasing the intracellular retinal level: one would consist in saturating the plasma membrane of the cell with high concentrations of extracellular retinol, which would eventually enter into the cell; a better possibility consists in using the intracellular biosynthesis of retinol via a precursor (for example retinal) which enters the cell more easily. The presence of free (unesterified) retinol in the cell is very important. In effect, it may modulate genomic transcription via its nuclear receptors. It could also act at the plasma membrane so as to activate a second messenger, as has been suggested.

It seems that the entry of extracellular retinoic acid into the cell is not as finely controlled as that of retinol. However, RA induces undesirable side effects. The Applicant has shown that an exogenous supply of retinal may make the synthesis of endogenous RA possible, without inducing these effects.

EXAMPLE 3: APPLICATION IN THE CASE OF ROSACEA

This test was carried out on 10 subjects displaying the clinical signs of rosacea. A topical application containing 0.1% of retinal was used in daily application for 3 months.

Results

The results were very clear: in 6 of the 10 cases, a substantial improvement in the rosacea is observed from the first month. After treatment for 3 months, 70% of the subjects treated are left with almost no sign of characteristic erythrosis of rosacea.

EXAMPLE 4: APPLICATION IN THE CASE OF SEBORRHEIC DERMATITIS

This test was carried out on 10 subjects displaying the clinical signs of seborrheic dermatitis.

A topical application containing 0.05% of retinal was used in daily application for one month.

Results

After treatment for one month, 80% of the subjects treated are left with almost no characteristic signs of seborrheic dermatitis.

We claim:

1. A dermatological and/or cosmetological composition comprising at least one retinoid of formula (I)

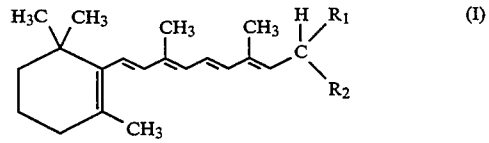

in which:

$R_1$ and $R_2$ independently represent

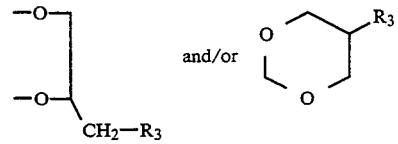

and/or or $R_1$ and $R_2$ together represent a double bond with a nitrogen atom so as to form an imine group of formula $=N-R_4$, $R_3$ represents a hydrogen atom, a hydroxyl group or an acyloxy group having 5 carbon atoms, $R_4$ represents a group chosen from

or $$(CH_2)_n-C(=O)-N(R_6)(R_7) \quad OR \quad -(CH_2)_n-C(=O)-O-R_8$$

with n ranging from 0 to 5, $R_5$ represents a hydrogen atom, or a lower alkyl group having 1 to 5 carbon atoms or a lower acyl group having 1 to 5 carbon atoms, $R_6$ and $R_7$ independently represent a hydrogen atom or a lower alkyl group having 1 to 5 carbon atoms, and $R_8$ represents a hydrogen atom or a lower alkyl group having 1 to 5 carbon atoms.

2. A composition according to claim 1, wherein the retinoid is of formula (II)

[Structure (II): retinoid with cyclic acetal ending in CH$_2$OH]

3. A composition according to claim 1 wherein the retinoid is of the formula (III)

[Structure (III): retinoid with cyclic acetal ending in CH$_2$-O-C(=O)-CH$_3$]

4. A composition according to claim 1 wherein the retinoid is of the formula (IV)

[Structure (IV): retinoid with glyceryl acetal ending in OH]

5. A method of treating a patient in need of such treatment comprising administering a composition of claim 1 to treat a disease selected from the group consisting of psoriasis, acne, aczema, rosacea, actinic keratosis, seborrheic dermatitis, and congenital keratinization disorders.

6. A stomatological composition according claim 1 characterized in that it contains from 0.01 to 5% of the retinoid of formula I in a pharmaceutically acceptable vehicle.

7. A cosmetological composition according to claim 1 characterized in that it contains from 0.01 to 5% of the retinoid of formula I, in a cosmetologically acceptable vehicle.

8. Composition according to claim 1, characterized in that it contains a compound which forms an imine function with aminoethanol, of formula (V)

[Structure (V): retinylidene imine C=N-CH$_2$-CH$_2$-OH]

9. Composition according to claim 1 characterized in that it contains the compound which forms an imine function with glycinamide of formula (VI)

[Structure (VI): retinylidene imine C=N-CH$_2$-C(=O)-NH$_2$]

10. Dermatological composition according to claim 1, characterized in that it contains 0.01 to 5% of at least one retinoid, in a pharmaceutically acceptable vehicle.

11. A method of treating rosacea or seborrheic dermatitis comprising administering to a patient in need of such treatment a therapeutically effective amount of a retinoid of formula (I)

[Structure (I): retinoid with terminal C(R$_1$)(R$_2$)]

in which:

$R_1$ and $R_2$ independently represent $$-O-\underset{CH_2-R_3}{\overset{}{|}}-O- \quad \text{and/or} \quad \text{[cyclic acetal with } R_3\text{]}$$

or $R_1$ and $R_2$ together represent a double bond with an oxygen atom, or with a nitrogen atoms so as to form an imine group of formula $=N-R_4$, $R_3$ represents a hydrogen atom, a hydroxyl group or an acyloxy group having 5 carbon atoms, $R_4$ represents a group chosen from:

$$-CH_2-(CH_2)_n-O-R_5,$$

or $$(CH_2)_n-C(=O)-N(R_6)(R_7) \quad OR \quad -(CH_2)_n-C(=O)-O-R_8$$

with n ranging from 0 to 5, $R_5$ represents a hydrogen atom, a lower alkyl group having 1 to 5 carbon atoms or a lower acyl group having 1 to 5 carbon atoms, $R_6$ and $R_7$ independently represent a hydrogen atom or a lower alkyl group having 1 to 5 carbon atoms, and $R_8$ represents a hydrogen atom or a lower alkyl group having 1 to 5 carbon atoms.

12. A method as in claim 11 wherein $R_1$ and $R_2$ together represent a double bond with an oxygen atom.

13. A method as in claim 11 wherein from 0.01 to 5% of the retinoid in a pharmaceutically acceptable vehicle is administered to said patient.

14. A method as in claim 13 wherein from 0.1 to 1% of the retinoid is administered to said patient.

* * * * *

UNITED STATES PATENT AND TRADEMARK OFFICE
CERTIFICATE OF CORRECTION

PATENT NO. : 5,438,073

DATED : August 1, 1995

INVENTOR(S) : Saurat, et al

It is certified that error appears in the above-indentified patent and that said Letters Patent is hereby corrected as shown below:

Column 4, line 63, insert the word —OR—.

Column 8, line 16, delete [AND/NADH, RAL] and insert —NAD/NADH,RAL—.

Column 8, line 27, delete [AND/NADH, RAL] and insert —NAD/NADH,    —.

UNITED STATES PATENT AND TRADEMARK OFFICE
CERTIFICATE OF CORRECTION

PATENT NO. : 5,438,073
DATED : August 1, 1995
INVENTOR(S) : Saurat, et al

It is certified that error appears in the above-indentified patent and that said Letters Patent is hereby corrected as shown below:

Column 10, please delete

[
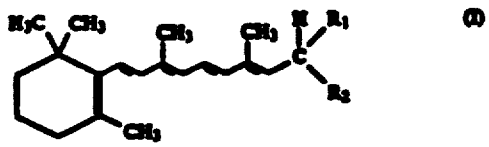
]

and insert

--
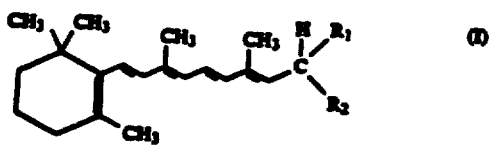
--

Signed and Sealed this

Twenty-first Day of November, 1995

Attest:

BRUCE LEHMAN

Attesting Officer    Commissioner of Patents and Trademarks